United States Patent [19]

Kuo

[11] Patent Number: 5,346,912
[45] Date of Patent: Sep. 13, 1994

[54] 2-CYANO-3-HYDROXY-(N-PYRIDYL)-PROPENAMIDE COMPOUNDS

[75] Inventor: Elizabeth A. Kuo, Swindon, England

[73] Assignee: Roussel-Uclaf, France

[21] Appl. No.: 170,372

[22] Filed: Dec. 20, 1993

[30] Foreign Application Priority Data

Jan. 5, 1993 [GB] United Kingdom ............... 9300083.4

[51] Int. Cl.$^5$ .................... C07D 213/02; A61K 31/44
[52] U.S. Cl. .................... 514/352; 546/115; 546/289; 546/297; 546/309; 514/302; 514/344; 514/345; 514/348; 514/349
[58] Field of Search ............... 546/309, 115, 289, 297; 514/352, 302, 344, 345, 348, 349

[56] References Cited

U.S. PATENT DOCUMENTS 4,435,407 3/1984 Walker .................. 548/195
5,240,960 8/1993 Hambleton .................. 514/521

FOREIGN PATENT DOCUMENTS 0372470 12/1989 European Pat. Off. ............ 548/195
9117748 11/1991 PCT Int'l Appl. .................. 546/309

OTHER PUBLICATIONS

Chemical Abstracts, vol. 119, No. 3, Abstract 27, 839t, Jul. 19, 1993 (=Eur. Patent 533573A2, Mar. 24, 1993). Search Report No. EP 94 40 0009–Journal of Chemical Soc. Perkin Trans. 1 (1972) Novel Immunosuppressive Butenamides, pp. 2203–2213, Axton, et al.

Primary Examiner—C. Warren Ivy
Assistant Examiner—Zinna N. Davis
Attorney, Agent, or Firm—Bierman and Muserlian

[57] ABSTRACT

A compound selected from the group consisting of a compound of the formula

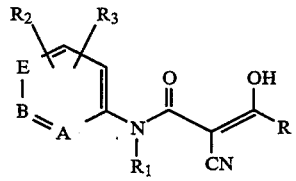

wherein A, B and E are individually selected from the group consisting of $=CH-$ and $=N-$ with at least one being $=N-$, R is selected from the group consisting of cycloalkyl of 3 to 6 carbon atoms, and alkenyl and alkynyl of 2 to 6 carbon atoms, $R_1$ is hydrogen or alkyl of 1 to 3 carbon atoms, $R_2$ and $R_3$ together are $-O-CH_2-O-$ or are individually selected from the group consisting of hydrogen, halogen, $-NO_2$, $-CN$, alkyl, alkylthio and alkoxy of 1 to 6 carbon atoms, cycloalkyl of 3 to 6 carbon atoms, $-COR_4$, $-(CH_2)_m-CX_3$, $-O-(CH_2)_m-CX_3$, $-S-(CH_2)_m-CX_3$, $-O-(CX_2)_m-CX_3$ and $-S-(CX_2)_m-CX_3$, $R_4$ is hydrogen or alkyl or cycloalkyl of up to 6 carbon atoms, X is halogen and m is 0, 1, 2 or 3 and their addition salts with a non-toxic, pharmaceutically acceptable base having anti-flammatory and immulodulatory activity and their preparation.

10 Claims, No Drawings

2-CYANO-3-HYDROXY-(N-PYRIDYL)-PROPENAMIDE COMPOUNDS

OBJECTS OF THE INVENTION

It is an object of the invention to provide the novel compounds of formula I and their non-toxic, pharmaceutically acceptable salts and a process for their preparation.

It is another object of the invention to provide novel anti-inflammatory compositions and a method of treating inflammation in warm-blooded animals.

These and other objects and advantages of the invention will become obvious from the following detailed description.

THE INVENTION

The novel propenamides of the invention are selected from the group consisting of a compound of the formula

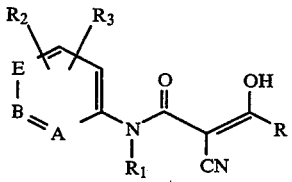

wherein A, B and E are individually selected from the group consisting of =CH— and =N— with at least one being =N—, R is selected from the group consisting of cycloalkyl of 3 to 6 carbon atoms, and alkenyl and alkynyl of 2 to 6 carbon atoms, $R_1$ is hydrogen or alkyl of 1 to 3 carbon atoms, $R_2$ and $R_3$ together are —O—$CH_2$—O— or are individually selected from the group consisting of hydrogen, halogen, —$NO_2$, —CN, alkyl, alkylthio and alkoxy of 1 to 6 carbon atoms, cycloalkyl of 3 to 6 carbon atoms, —$COR_4$, —$(CH_2)_m$—$CX_3$, —O—$(CH_2)_m$—$CX_3$, —S—$(CH_2)_m$—$CX_3$, —O—$(CX_2)_m$—$CX_3$ and —S— $(CX_2)_m$—$CX_33$, $R_4$ is hydrogen or alkyl or cycloalkyl of up to 6 carbon atoms, X is halogen and m is 0, 1, 2 or 3 and their addition salts with a non-toxic, pharmaceutically acceptable base. The compounds may be in any tautomeric form of formula I.

Examples of alkyl of 1 to 3 carbon atoms are methyl, ethyl, n-propyl and isopropyl and examples of alkyl of 1 to 6 carbon atoms include methyl, ethyl, n-propyl, isopropyl and linear or branched butyl, pentyl and hexyl. Example of cycloalkyl of 3 to 6 carbon atoms are cyclopropyl, cyclobutyl, cyclopentyl and cyclohexyl and examples of halogen are fluorine, chlorine, bromine and iodine. Preferred are fluorine, chlorine and bromine.

Alkoxy and alkylthio of 1 to 6 carbon atoms are methoxy, ethoxy, n-propoxy, isopropoxy, linear or branched butoxy, pentyloxy and hexyloxy, methylthio, ethylthio, n-propylthio, isopropylthio and branched or linear butylthio, pentylthio and hexylthio. Examples of alkenyl of 2 to 6 carbon atoms are

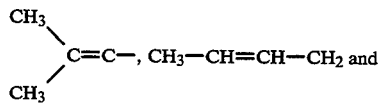

-continued
$CH_3$—$CH_2$—CH=CH—.

Examples of alkynyl of 2 to 6 carbon atoms is $CH_3$—C≡C—.

Examples of —$(CH_2)_m$—$CX_3$, —O—$(CH_2)_m$—$CX_3$, —S—$(CH_2)_m$—$CX_3$, —O—$(CX_2)_m$—$CX_3$ and —S—$(CX_2)_m$—$CX_3$ in which m is 0, 1, 2 or 3 are —$CF_3$, —$CH_2$—$CF_3$, —$(CH_2)_2$—$CF_3$, —$(CH_2)_3$—$CF_3$, —O—$CF_3$, —O—$CH_2$—$CF_3$, —O—$(CH_2)_2$—$CF_3$, —O—$(CH_2)_3$—$CF_3$, —S—$CF_3$, —S—$CH_2$—$CF_3$, —S—$(CH_2)_2$—$CF_3$, —S—$(CH_2)_3$—$CF_3$, —O—$CF_2$—$CF_3$, —S—$CF_2$—$CF_3$.

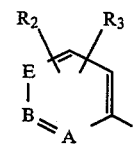

are N-(2-chloropyrid-5-yl)-, N-(4-methyl-5-nitropyrid-2-yl)-, N-(5-trifluoromethylpyrid-2-yl)-, N-(5-chloropyrid-2-yl)-, N-(5-bromo-pyrid-2-yl)-, N-(5-nitropyrid-2-yl)-, N-(pyrid-4-yl)- and N-(3,5-dichloropyrid-2-yl)-.

The base addition salts can be salts with inorganic or organic bases such as sodium, potassium, lithium, calcium, magnesium and ammonium salts, or salts formed with organic bases such as methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine.

Among the preferred compounds of formula I are those wherein R is cyclopropyl or

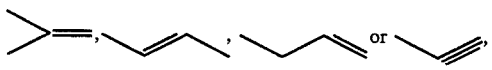

those wherein $R_1$ is hydrogen or methyl, those wherein $R_2$ and $R_3$ are individually selected from the group consisting of hydrogen, chlorine, bromine, —CN, —$NO_2$, methyl, methoxy, cyclopropyl, methylthio, —$COR_4$, —$(CH_2)_m$—$CF_3$, —O—$(CH_2)_m$—$CF_3$, —S—$(CH_2)_m$—$CF_3$, —O—$(CF_2)_m$—$CF_3$ and —S—$(CF_2)_m$—$CF_3$, $R_4$ is hydrogen or methyl or cyclopyropyl and m is 0, 1, 2 or 3 or $R_2$ and $R_3$ together are —O—$CH_2$—O—.

More preferred are the compounds of formula I wherein R is cyclopropyl, $R_1$ is hydrogen or methyl and $R_2$ and $R_3$ are individually hydrogen, chlorine, bromine, methyl, nitro or —$CF_3$.

Specific preferred compounds of formula I are
2-cyano-3-cyclopropyl-3-hydroxy-N-(2-chloropyrid-5-yl)-2-propenamide;
2-cyano-3-cyclopropyl-3-hydroxy-N-(4-methyl-5-nitropyrid-2-yl)-2-propenamide;
2-cyano-3-cyclopropyl-3-hydroxy-N-(5-trifluoromethyl-pyrid-2-yl)-2-propenamide;
2-cyano-3-cyclopropyl-3-hydroxy-N-(5-chloropyrid-2-yl)-2-propenamide;
2-cyano-3-cyclopropyl-3-hydroxy-N-(5-bromopyrid-2-yl)-2-propenamide;
2-cyano-3-cyclopropyl-3-hydroxy-N-(5-nitropyrid-2-yl)-2propenamide;

2-cyano-3-cyclopropyl-3-hydroxy-N-(pyrid-4-yl)-2-propenamide;

2-cyano-3-cyclopropyl-3-hydroxy-N-(3,5-dichloropyrid-2-yl)-2-propenamide; and their base addition salts.

A process for the preparation of the compounds of formula I comprises reacting a compound of the formula

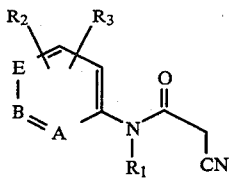

wherein A, B, E, $R_1$, $R_2$ and $R_3$ are as defined above with sodium hydride optionally in the presence of a catalyst and reacting the resulting product with a compound of the formula

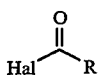

wherein Hal is halogen and R is as defined above; or b reacting a compound of formula II with a compound of the formula

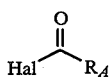

wherein Hal is halogen and $R_A$ is R as defined above additionally carrying a protecting group to obtain a compound of the formula

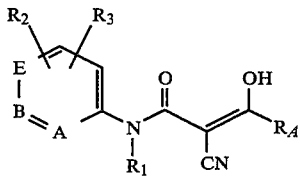

wherein $R_A$, A, B, E, $R_1$, $R_2$ and $R_3$ are as defined above and cleaving the protecting group to obtain a compound of formula I in which R is as defined above.

Compounds of formula I wherein R is cycloalkyl of 3 to 6 carbon atoms may additionally be prepared by reacting a compound of the formula

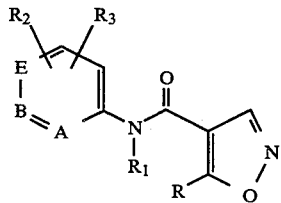

in which A, B, E, R, $R_1$, $R_2$ and $R_3$ are as defined above with a strong base.

In the above processes, the compound of formula I thereby obtained may then be converted into a base addition salt thereof by conventional methods.

The reaction between the compound of formula II and sodium hydride is preferably effected in the presence of an anhydrous organic solvent such as tetrahydrofuran or dichloromethane and optionally in the presence of a catalyst capable of solvating the sodium hydride such as imidazole.

The reaction between the product of the reaction of the compound of formula II and sodium hydride and the compound of formula III or $III_A$ is preferably effected in the presence of an anhydrous organic solvent such as tetrahydrofuran or dichloromethane, at ambient or low temperature. In some cases, the optimum temperature will be about 25° C. and in others, in the region of 0° C. In others, the optimum temperature will be between −80° C. and −50° C.

The compound of formula III or $III_A$ is preferably an acid chloride or acid fluoride and an example of the compound of formula III is propynyl fluoride which may be prepared by reaction of propiolic acid with benzoyl fluoride and distillation of the subsequent reaction mixture.

Where $R_A$ is R additionally carrying a protecting group, this protecting group may be an arylseleno such a phenylseleno. The deprotection of such a protecting group may be carried out by oxidation using a peroxide such as hydrogen peroxide, either in the absence of a solvent or in the presence of a mixture of organic solvents such as methanol/dichloromethane. The reaction between the compound of formula IV and a strong base is preferably effected at reflux temperature of the reaction medium.

The compounds of formula II may be prepared by reacting a compound of the formula

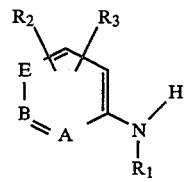

in which A, B, E, $R_1$, $R_2$ and $R_3$ are as defined above with cyanoacetic acid in the presence of dicyclohexylcarbodiimide or phosphorous pentachloride in the presence of an anhydrous organic solvent such as tetrahydrofuran or dichloromethane. The reaction in the presence of both dicyclohexylcarbodiimide and anhydrous tetrahydrofuran is denoted Method A in the subsequent experimental description. The reaction in the presence of both phosphorous pentachloride and anhydrous dichloromethane is denoted Method B in the experimental description.

The compounds of formula IV may be prepared by reaction of a compound of formula V as defined above with an acid chloride of the formula

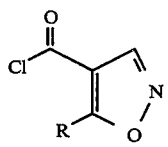

according to a process analogous to that described in WO91/17748.

The acid chloride of formula VI can be prepared from the corresponding acid which may be prepared by processes described in the literature; particularly European Patent No. 326,107.

The compounds of formula I are acidic in character and the base addition salts of the compounds of formula I can advantageously be prepared by reacting, in approximately stoichiometric proportions an inorganic or organic base with the compound of formula I. The salts can be prepared without intermediate isolation of the corresponding acidic compound.

The novel anti-flammatory compositions of the invention are comprised of an anti-flammatorily effective amount of a compound of formula I or its base salts and an inert pharmaceutical carrier. The compositions may be in the form of tablets, dragees, capsules, granules, suppositories or injectable solutions or suspensions.

Examples of inert pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions have a remarkable anti-flammatory activity and inhibit both the flammatory response cause by irritant agents, and delayed hypersensitivity reactions, by hindering activation of the immune cells by a specific antigen. They are useful for the treatment of rheumatoid arthritis, chronic inflammatory diseases of immune or non-immune origin (e.g. graft-versus-host disease, transplantation reactions, uveitis) and cancer.

The novel method of invention for treating inflammation in warm-blooded animals, including humans, comprises administering to warm-blooded animals, an anti-inflammatory effective amount of a compound of formula I or a non-toxic, pharmaceutically acceptable base salt thereof. The compounds may be administered orally, rectally or parenterally. The usual dose is 0.0013 to 2.66 mg/kg depending on the condition treated, the method of administration and the specific compounds.

In the following examples, there are described several preferred embodiments to illustrate the invention. However, it should be understood that the invention is not intended to be limited to the specific embodiments.

PREPARATION OF STARTING MATERIALS FOR EXAMPLES 1-8

Starting material of 2-cyano-3-cyclopropyl-3-hydroxy-N-2-chloropyrid-5-yl)-2-propenamide (example 1)

METHOD A 5.95 g (70.0 mmol) of cyanoacetic acid and 14.44 g (70.0 mmol) of dicyclohexylcarbodiimide were added to a stirred solution of 9.00 g (70.0 mmol) of 5-amino-2-chloropyridine in 150 ml of anhydrous tetrahydrofuran at 0° C. The reaction was monitored by thin layer chromatography and when complete, the reaction mixture was filtered and the filtrate was evaporated to dryness. The resulting solid was triturated with anhydrous dichloromethane, filtered and dried in vacuo to obtain 10.5 g of N-(2-chloropyrid-5-yl)-2-cyanoacetamide (77% yield).

The starting materials for the following examples were made according to this method from the appropriate substituted 2-amino pyridine with the modification indicated below:

Starting material for 2-cyano-3-cyclopropyl-3-hydroxy-N-(4-methyl-5-nitro-pyrid-2-yl) -2-propenamide (example 2)

The product was purified by column chromatography (Sorbsil C60 silica, 60% hexane/40% ethyl acetate) to obtain a 51% yield of N-(4-methyl-5-nitropyrid-2-yl)-2-cyanoacetamide.

Starting material for 2-cyano-3-cyclopropyl-3-hydroxy-N-(5-trifluoromethylpyrid-2-yl)-2-propenamide (example 3)

The reaction was carried out using 1.2 equivalents of cyanoacetic acid and 1.2 equivalents of dicyclohexylcarbodiimide to obtain a 79% yield of N-(5-trifluoromethylpyrid-2-yl) -2-cyanoacetamide.

Starting material for 2-cyano-3-cyclopropyl-3-hydroxy-N-(5-chloropyrid-2-yl)-2-propenamide (example 4)

The reaction was carried out using 1 equivalent of cyanoacetic acid and 1.1 equivalents of cicyclohexylcarbodiimide in dichloromethane at reflux. Trituration with ethyl acetate give a 90% yield of N-(5-chloropyrid-2-yl)-2-cyanoacetamide.

Starting material of 2-cyano-3-cyclopropyl-3-hydroxy-N-(5-bromo-pyrid-2-yl)-2-propenamide (example 5)

METHOD B 0.22 g (2.60 mmol) of cycanoacetic acid were added to a stirred solution of 0.54 g (2.60 mmol) of phosphorus pentachloride in 8 ml of anhydrous dichloromethane over a period of 1 minute. The resulting solution was refluxed for 30 minutes and then the reaction vessel was flushed through with nitrogen. 0.30 g (1.73 mmol) of 2-amino-5-bromopyridine were added and reflux was continued. The reaction was monitored by thin layer chromatography and when complete, the reaction mixture was poured into 4 ml of water. After stirring for 30 minutes, N-(5-bromopyrid-2-yl)-2-cyanoacetamide was filtered off and dried in vacuo to obtain 0.27 g (65% yield) of the desired product.

Starting material for 2-cyano-3-cyclopropyl-3-hydroxy-N-(5-nitro-pyrid-2-yl)-2-propenamide (example 6)

N-(5-nitropyrid-2-yl)-2-cyanoacetamide was obtained from 2-amino 5-nitro-pyridine using method B in a 42% yield Starting material for 2-cyano 3-cyclopropyl 3-hydroxy N-(3,5-dichloropyrid-2-yl) 2-propenamide (example 8)

N-(3,5-dichloropyrid-2-yl)-2-cyano acetamide was obtained from 2-amino-3,5-dichloropyridine by method B in a 29% yield.

PREPARATION OF EXAMPLES 1-8

Example 1: 2-cyano-3-cyclopropyl-3-hydroxy-N-(2-chloropyrid-5-yl)-2-propenamide

METHOD C 3.21 of (80% dispersion in mineral oil, 107.1 mmol) of sodium hydride were added portionwise to a stirred solution of 7.00 g (35.7 mmol) of N-(2-chloropyrid-5-yl)-2-cyanoacetamide in 200 ml of anhydrous tetrahydrofuran at 0° C. After stirring for one hour, 48.6 ml (53.6 mmol) of cyclopropanecarbonyl chloride were added. The progress of the reaction was followed by thin layer chromatography and when complete, the reaction mixture was added to 1.25 l of water, acidified to a pH of 1 by the addition of 35% hydrochloric acid and then was stirred for 30 minutes. The resulting precipitate was filtered off and washed with water, then triturated with ethyl acetate, filtered and dried in vacuo to obtain 7.91 g, (83% yield) of the desired product.

The examples were made by the method of Example 1 with the modifications indicated:

Example 2:
2-cyano-3-cyclopropyl-3-hydroxy-N-(4-methyl-5-nitro-pyrid-2-yl)-2-propenamide Crystallized from ethyl acetate/hexane in 87% yield.

Example 3:
2-cyano-3-cyclopropyl-3-hydroxy-N-(5-trifluoromethyl-pyrid-2-yl)-2-propenamide Crystallized from ethyl acetate/40%-60% petroleum ether in an 86% yield.

Example 4:
2-cyano-3-cyclopropyl-3-hydroxy-N-(5-chloropyrid-2-yl)-2-propenamide

The reaction was carried out using 2.4 equivalents of sodium hydride with a catalytic amount of imidazole and 1.2 equivalents of cyclopropane-carbonyl chloride. Crystallization from ethyl acetate gave a 91% yield of the desired compound.

Example 5:
2-cyano-3-cyclopropyl-3-hydroxy-N-(5-bromopyrid-2-yl)-2-propenamide

The reaction was carried out using 2.4 equivalents of sodium hydride with a catalytic amount of imidazole and 1.2 equivalents of cyclopropanecarbonyl chloride at 25° C. The desired compound was triturated with diethyl ether, filtered and dried in vacuo to obtain an 83% yield of the product.

Example 6:
2-cyano-3-cyclopropyl-3-hydroxy-N-(5-nitropyrid-2-yl)-2-propenamide

The reaction was carried out using 2.4 equivalents of sodium hydride with a catalytic amount of imidazole and 1.2 equivalents of cyclopropanecarbonyl chloride at 25° C. The compound was triturated with diethyl ether, filtered and dried in vacuo to obtain an 89% yield of the desired product.

Example 7:
2-cyano-3-cyclopropyl-3-hydroxy-N-(pyrid-4-yl)-2-propenamide

METHOD D 1.5 g (9.75 mmol) of 5-cyclopropylisoxazole-4-carboxylic acid prepared as described in EP 326,107 and 20 ml of thionyl chloride were refluxed together for 90 minutes. The reaction mixture was evaporated in vacuo and the residue was co-evaporated with toluene. The resulting acid chloride was dissolved in 10 ml of anhydrous dichloromethane and the solution was added to 1.0 g (6.5 mmols) of 4-aminopyridine suspended in 50 ml of anhydrous dichloromethane. 0.77 g (9.75 mmol) of pyridine were added and the reaction mixture was stirred at room temperature for 90 minutes. The solid product was filtered off, dissolved in 100 ml of methanol and 2 ml of triethylamine were added. The reaction mixture was refluxed for one hour, then poured into 200 ml of water and acidified to a pH of 1 by addition of conc. hydrochloric acid. Standing at 4° C. for sixteen hours yielded the title compound as a crystalline solid which was washed with water and dried in vacuo to obtain 0.67 g, (45% yield) of the desired product.

Example 8:
2-cyano-3-cyclopropyl-3-hydroxy-N-(3,5-dichloro-pyrid-2-yl)-2-propenamide was prepared from N-(3,5-dichloropyrid-2-yl)-2-cyano-acetamide by method C as described in Example 1 for a 69% yield of the desired compound.

Spectral data, yields, melting points and analytical data for the Examples are given in Table I.

TABLE 1

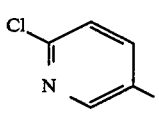

| Ex | Ar | Method | m.pt °C. | IR cm$^{-1}$ | $^1$H NMR δ | Formula M. wt | Analysis % Calc Found | | | |
|----|----|--------|----------|--------------|-------------|---------------|------|------|------|------|
|    |    |        |          |              |             |               | C    | H    | N    | X    |
| 1  | Cl-pyridyl | A + C | 196–198 | 3280, 2195, 1560, 1515, 1455, 1275, 1110, 975, 885. | CDCl$_3$ 15.59(s, 1H, O—H); 8.51(d, J=2.5Hz, 1H, Ar—H); 8.00(s, dd, J=8.5Hz, 2.5Hz, 2H, N—H, Ar—H); 7.33(d, J=8.5Hz, 1H, Ar—H); 2.14(m, 1H, cyclopropyl-H); 1.29(m, 4H, cyclopropyl-H). | C$_{12}$H$_{10}$ClN$_3$O$_2$ 263.69 | 54.66 | 3.82 | 15.94 | 13.45 |

TABLE 1-continued $$\text{Ar}\diagdown\underset{H}{N}\diagdown\underset{\underset{CN}{|}}{C}\diagdown\underset{O}{\overset{O}{\|}}\diagdown\text{cyclopropyl} \rightleftharpoons \text{Ar}\diagdown\underset{H}{N}\diagdown\underset{\underset{CN}{|}}{C}=\underset{OH}{C}\diagdown\text{cyclopropyl}$$

| Ex | Ar | Method | m.pt °C. | IR cm$^{-1}$ | $^1$H NMR δ | Formula M. wt | Analysis % Calc Found | | | |
|---|---|---|---|---|---|---|---|---|---|---|
| | | | | | | | C | H | N | X |
| 2 | 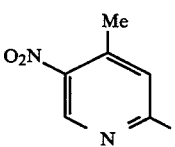 4-Me, 5-O$_2$N, 2-Me pyridine | A + C | 178 | (3400–2000)br, 3250, 2210, 1603, 1495, 1330, 1095, 985, 765. | DMSO-d$_6$ 13.34(brs, 1H, O—H); 11.86(vbrs, 1H, N—H); 8.94(s, 1H, Ar—H); 8.22(s, 1H, Ar—H); 2.57 (m, 3H, Ar—Me); 2.22(m, 1H, cyclopropyl-H); 0.79(m, 4H, cyclopropyl-H). | C$_{13}$F$_{12}$N$_4$O$_4$ 268.26 | 54.16 | 4.20 | 19.44 | |
| 3 | 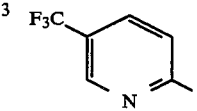 5-F$_3$C, 2-Me pyridine | A + C | 202–203 (decomposition) | 3395, 2205, 1635, 1580, 1520, 1395, 1325, 1125, 1075, 895. | CDCl$_3$ 15.38(brs, 1H, O—H); 8.60(s, 1H, Ar—H); 8.38(brs, 1H, N—H); 8.22(d, J=8.5Hz, 1H, Ar—H); 7.95(d, J=8.5Hz, 1H, Ar—H); 2.18(m, 1H, cyclopropyl-H); 1.29(m, 4H, cyclopropyl-H). | C$_{13}$H$_{10}$F$_3$N$_3$O$_2$ 297.23 | 52.53 | 3.39 | 14.14 | 19.18 |
| 4 | 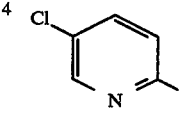 5-Cl, 2-Me pyridine | A + C | 223–225 | (3600–2800)br, 3385, 2180, 1590, 1555, 1505, 1405, 1370, 1280, 1000, 760. | DMSO-d$_6$ 12.59(s, 1H, N—H); 8.24(m, 2H, Ar—H); 7.77(dd, J=9.0Hz, 2.5Hz, 1H, Ar—H); 2.20(m, 1H, cyclopropyl-H); 0.71(m, 4H, cyclopropyl-H). | C$_{12}$H$_{10}$ClN$_3$O$_2$ 263.69 | 54.66 54.42 | 3.82 3.91 | 15.94 15.69 | 13.45 |
| 5 | 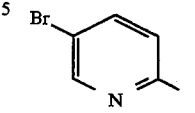 5-Br, 2-Me pyridine | B + C | 202–203 | (3300–1800)br, 3110, 2200, (1650–1530)br, 1145, 1005, 980, 770, 720. | CDCl$_3$ 13.00(brs, 1H, N—H); 8.36(d, J=2Hz, 1H, Ar—H); 8.07(m, 2H, Ar—H); 2.21(m, 1H, cyclopropyl-H); 0.79(m, 4H, cyclopropyl-H). | C$_{12}$H$_{10}$BrN$_3$O$_2$ 308.14 | 46.78 46.63 | 3.27 3.33 | 13.64 13.19 | 25.93 25.71 |
| 6 | 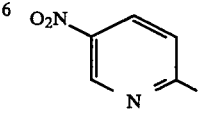 5-O$_2$N, 2-Me pyridine | B + C | 163–165 | (3400—1850)br, 3360, 2195, 1630, 1600, 1545, 1490, 1340, 1300, 980, 885, 630. | DMSO-d$_6$ 13.17(s, 1H, N—H); 9.07(d, J=3.0Hz, 1H, ArH); 8.50(dd, J=9.0Hz, 1H, Ar—H); 8.38(d, J=9.0Hz, 1H, Ar—H); 2.22(m, 1H, cyclopropyl-H); 0.77(m, 4H, cyclopropyl-H). | C$_{12}$H$_{10}$N$_4$O$_4$ 274.24 | 52.56 52.21 | 3.68 3.70 | 20.43 20.35 | |
| 7 | 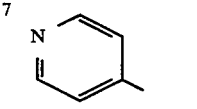 4-Me pyridine | D | >300 | (3600–2200)br, 3430, 2180, 1630, 1225, 1185, 1110, 985, 815. | DMSO-d$_6$ 14.17(brs, 1H, O—H); 13.51(s, 1H, N—H); 8.53(d, J=7.0Hz, 2H, Ar—H); 8.04(d, J=7.0Hz, 2H, Ar—H); 2.25(m, 1H, cyclopropyl-H); 0.80(m, 4H, cyclopropyl-H). | C$_{12}$H$_{11}$N$_2$O$_2$ 229.24 | 62.87 | 4.48 | 18.33 | |

TABLE 1-continued

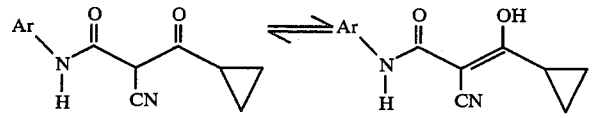

| Ex | Ar | Method | m.pt °C. | IR cm$^{-1}$ | $^1$H NMR δ | Formula M. wt | Analysis % Calc Found C | H | N | X |
|---|---|---|---|---|---|---|---|---|---|---|
| 8 | Cl-pyridine (3,6-dimethyl) | B + C | 222-224 | 3080, 3005, 2190, 1630, 1525, 1430, 1405, 1220, 1105, 990, 885. | DMSO-d$_6$ 13.76(br s, 1H, OH); 9.50-11.0(br s, 1H, NH); 8.62(d, J=1.6Hz, 1H, Ar—H); 8.42(d, 1H, Aryl-H); 2.22(m, 1H, cyclopropyl-H); 0.88(m, 4H, cyclopropyl-H). | C$_{12}$H$_9$Cl$_2$N$_3$O$_2$ 296.12 | 48.34 48.47 | 3.04 3.18 | 14.09 13.89 | 23.79 23.68 |

Example 9: Tablets were prepared containing 20 mg of the compound of Example 1 or 2 and sufficient excipient of lactose, starch, talc and magnesium stearate for a tablet of 150 mg.

PHARMACOLOGICAL ACTIVITY

Test 1: Carrageenan rat paw oedema (PO-R)

One hour after the oral administration of the test compounds or control vehicle to groups 6 to 12 male rats (CFHB, weight range 160-180 g), 1 mg of carrageenan dissolved in 0.2 ml of saline was injected into the right hind foot pad. Contralateral paws received control saline injections and paw oedema responses were assessed three hours later.

Test 2: Delayed type hypersensitivity mouse paw oedema

Groups of 8 to 10 male mice (CD-1. weight range 25-30 g) were sensitized by the subcutaneous injection of 1 mg of methylated bovine serum albumin (MBSA) in 0.2 ml volumes of saline/Freund's complete adjuvant (FCA) emulsion. Negative control groups received injections of saline/FCA emulsion. DTH paw oedema responses were assessed twenty-four hours after the right hind foot pad challenge with 0.1 mg MBSA in 0.05 ml volumes of saline on day seven after sensitization. Contralateral paws received control saline injections. The test compounds or control vehicles were orally administered daily on days four, five, six and twice on day seven, one hour before and six hours after MBSA challenge.

Test 3: Delayed-type hypersensitivity rat paw oedema (DTH-R)

Groups of 8 to 12 male rats (CFHB, weight range 160-180 g) were sensitized by the subcutaneous tail base injection of 0.1 ml volumes of FCA. Negative control groups received injections of Freund's incomplete adjuvant. DTH paw oedema responses were assessed twenty-four hours after the right hind foot pad challenge with 0.1 mg of MBSA in 0.4 mg of Mycobacterium tuberculosis extract antigen in 0.2 ml volumes of saline on day seven after sensitization. Contralateral paws received control saline injections. The test compounds were orally administered daily on days four, five, six and twice on day seven, one hour before and six hours after antigenic challenge.

The results of these tests are given in Table II where the percentage inhibition of oedema formation is given. Doses are given in units of mg/kg p.o.

TABLE II

| | Test 1 | | Test 2 | | Test 3 | |
|---|---|---|---|---|---|---|
| Example | % inhibition | Dose | % inhibition | Dose | % inhibition | Dose |
| 1 | 32 | 50 | Toxic | 100 | 71 | 50 |
| | | | 9 | 30 | 8 | 10 |
| 2 | 10 | 50 | 7 | 100 | 48 | 50 |
| 3 | 30 | 10 | 37 | 30 | 88 | 10 |
| | | | | | 40 | 3 |
| 4 | 18 | 50 | 48 | 100 | 64 | 50 |
| 5 | 11 | 50 | Toxic | 100 | Toxic | 50 |
| | | | 4 | 30 | 66 | 10 |
| 6 | −6 | 50 | 27 | 100 | 67 | 50 |
| 7 | −43 | 50 | 22 | 100 | 18 | 50 |
| 8 | −15 | 50 | 9 | 100 | 21 | 50 |

Various modifications of the compounds and method of the invention may be made without departing from the spirit or scope thereof and it is to be understood that the invention is intended to be limited only as defined in the appended claims.

What is claimed is:

1. A compound selected from the group consisting of a compound of the formula

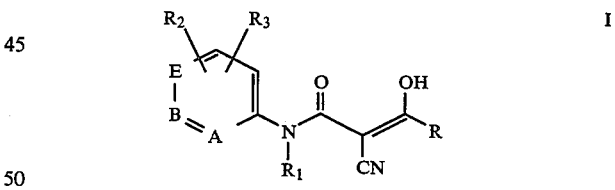

wherein two of A, B and E are =CH— and the third is =N—, R is selected from the group consisting of cycloalkyl of 3 to 6 carbon atoms, and alkenyl and alkynyl of 2 to 6 carbon atoms, R$_1$ is hydrogen or alkyl of 1 to 3 carbon atoms, R$_2$ and R$_3$ together are —O—CH$_2$—O— or are individually selected from the group consisting of hydrogen, halogen, —NO$_2$, —CN, alkyl, alkylthio and alkoxy of 1 to 6 carbon atoms, cycloalkyl of 3 to 6 carbon atoms, cycloalkyl of 3 to 6 carbon atoms, —COR$_4$, —(CH$_2$)$_m$—CX$_3$, —O—(CH$_2$)$_m$—CX$_3$, —S—(CH$_2$)$_m$—CX$_3$, —O—(CX$_2$)$_m$—CX$_3$ and —S—(CX$_2$)$_m$—CX$_3$, R$_4$ is hydrogen or alkyl or cycloalkyl of up to 6 carbon atoms, X is halogen and m is 0, 1, 2 or 3 and their addition salts with a non-toxic, pharmaceutically acceptable base.

2. A compound of claim 1 wherein R is a member of the group consisting of cyclopropyl or

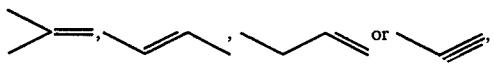

3. A compound of claim 1 wherein $R_1$ is hydrogen or methyl.

4. A compound of claim 3 wherein $R_2$ and $R_3$ are —OCH$_2$—O— or $R_2$ and $R_3$ are individually selected from the group consisting of hydrogen, chlorine, bromine, cyano, nitro, methyl, cyclopropyl, methoxy, methylthio, —CO—R$_4$, —(CH$_2$)$_m$—CF$_3$, —O—(CH$_2$)$_m$—CF$_3$, —S—(CH$_2$)$_m$—CF$_3$, —O—(CF$_2$)$_m$—CF$_3$ and —S—(CF$_2$)$_m$—CF$_3$, m is 0, 1, 2 or 3 and $R_4$ is hydrogen or methyl or cyclopropyl.

5. A compound of claim 1 wherein R is cyclopropyl, $R_1$ is hydrogen or methyl and $R_2$ and $R_3$ are individually selected from the group consisting of hydrogen, chlorine, bromine, methyl, —NO$_2$ and —CF$_3$.

6. A compound of claim 1 selected from the group consisting of 2-cyano-3-cyclopropyl-3-hydroxy-N-(2-chloropyrid-5-yl)-2-propenamide;

2-cyano-3-cyclopropyl-3-hydroxy-N-(4-methyl-5-nitropyrid-2-yl)-2-propenamide;

2-cyano-3-cyclopropyl-3-hydroxy-N-(5-trifluoromethyl-pyrid-2-yl)-2-propenamide;

2-cyano-3-cyclopropyl-3-hydroxy-N-(5-chloropyrid-2-yl)-2-propenamide;

2-cyano-3-cyclopropyl-3-hydroxy-N-(5-bromopyrid-2-yl)-2-propenamide;

2-cyano-3-cyclopropyl-3-hydroxy-N-(5-nitropyrid-2-yl)-2-propenamide;

2-cyano-3-cyclopropyl-3-hydroxy-N-(pyrid-4-yl)-2-propenamide;

2-cyano-3-cyclopropyl-3-hydroxy-N-(3,5-dichloropyrid-2-yl)-2-propenamide; and their base addition salts.

7. An anti-flammatory composition comprising an anti-flammatory effective amount of a compound of claim 1 and an inert pharmaceutical carrier.

8. A composition of claim 7 wherein the active compound is selected from the group consisting of 2-cyano-3-cyclopropyl-3-hydroxy-N-(2-chloropyrid-5-yl)-2-propenamide;

2-cyano-3-cyclopropyl-3-hydroxy-N-(4-methyl-5-nitropyrid-2-yl)-2-propenamide;

2-cyano-3-cyclopropyl-3-hydroxy-N-(5-trifluoromethyl-pyrid-2-yl)-2-propenamide;

2-cyano-3-cyclopropyl-3-hydroxy-N-(5-chloropyrid-2-yl)-2-propenamide;

2-cyano-3-cyclopropyl-3-hydroxy-N-(5-bromopyrid-2-yl)-2-propenamide;

2-cyano-3-cyclopropyl-3-hydroxy-N-(5-nitropyrid-2-yl)-2-propenamide;

2-cyano-3-cyclopropyl-3-hydroxy-N-(pyrid-4-yl)-2-propenamide;

2-cyano-3-cyclopropyl-3-hydroxy-N-(3,5-dichloropyrid-2-yl)-2-propenamide; and their base addition salts.

9. A method of relieving inflammation in warm-blooded animals comprising administering to warm-blooded animals an anti-inflammatorily effective amount of a compound of claim 1.

10. The method of claim 9 wherein the active compound is selected from the group consisting of 2-cyano-3-cyclopropyl-3-hydroxy-N-(2-chloropyrid-5-yl)-2-propenamide;

2-cyano-3-cyclopropyl-3-hydroxy-N-(4-methyl-5-nitropyrid-2-yl)-2-propenamide;

2-cyano-3-cyclopropyl-3-hydroxy-N-(5-trifluoromethyl-pyrid-2-yl)-2-propenamide;

2-cyano-3-cyclopropyl-3-hydroxy-N-(5-chloropyrid-2-yl)-2-propenamide;

2-cyano-3-cyclopropyl-3-hydroxy-N-(5-bromopyrid-2-yl)-2-propenamide;

2-cyano-3-cyclopropyl-3-hydroxy-N-(5-nitropyrid-2-yl)-2-propenamide;

2-cyano-3-cyclopropyl-3-hydroxy-N-(pyrid-4-yl)-2-propenamide;

2-cyano-3-cyclopropyl-3-hydroxy-N-(3,5-dichloropyrid-2-yl)-2-propenamide; and their base addition salts.

* * * * *